United States Patent
Yang et al.

(10) Patent No.: US 10,034,710 B2
(45) Date of Patent: Jul. 31, 2018

(54) COSMETIC INSTRUMENT CAPABLE OF READING MEMORY CARD

(71) Applicant: Shenzhen GOODWIND Technology Development Co., Ltd., Shenzhen, Guangdong (CN)

(72) Inventors: Ziming Yang, Guangdong (CN); Liu Yang, Guangdong (CN)

(73) Assignee: Shenzhen GOODWIND Technology Development Co., Ltd., Shenzhen (CN)

( * ) Notice: Subject to any disclaimer, the term of this patent is extended or adjusted under 35 U.S.C. 154(b) by 390 days.

(21) Appl. No.: 14/831,866

(22) Filed: Aug. 20, 2015

(65) Prior Publication Data

US 2016/0228184 A1 Aug. 11, 2016

(30) Foreign Application Priority Data

Feb. 7, 2015 (CN) .......................... 2015 1 0066325

(51) Int. Cl.
*A61H 7/00* (2006.01)
*A61B 18/18* (2006.01)
(Continued)

(52) U.S. Cl.
CPC .............. *A61B 18/18* (2013.01); *A45D 34/04* (2013.01); *A45D 34/06* (2013.01); *A61H 7/005* (2013.01); *A61H 23/0245* (2013.01); *A61H 99/00* (2013.01); *A61N 5/0616* (2013.01); *A61B 2018/1807* (2013.01); *A61H 2201/10* (2013.01); *A61H 2201/105* (2013.01); *A61H 2201/5015* (2013.01); *A61H 2201/5046* (2013.01);
(Continued)

(58) Field of Classification Search
CPC ...................... A61B 18/18; A61B 2018/1807; A45D 34/04; A45D 34/06; A61H 7/005; A61H 23/0245; A61H 99/00; A61H 2201/10; A61H 2201/105; A61H 2201/5015; A61H 2201/5046; A61N 5/0616; A61N 1/044; A61N 1/328; A61N 2005/0626; A61N 2005/0644; A61N 2005/0651; A61N 2005/0663
USPC .......................................... 601/15, 131, 154
See application file for complete search history.

(56) References Cited

U.S. PATENT DOCUMENTS 3,733,634 A * 5/1973 Golbe .................... A46B 13/02
15/28
5,131,384 A * 7/1992 Obagi .................... A61H 15/02
401/28
(Continued)

*Primary Examiner* — Andrew S Lo

(57) ABSTRACT

A cosmetic instrument capable of reading a memory card includes a first housing; a second housing, assembled with the first housing to cooperatively form a shell having a chamber; a massage head mounted on a first end of the shell, the massage head extending into the chamber; a control panel comprising a display panel, the control panel being mounted on the shell beside the massage head; a micro controller unit and a drive unit positioned in the chamber and electrically connected with each other, the micro controller unit being electrically connected to the control panel and the display panel. The first housing and the seconding housing define a card insertion hole. The micro controller unit is configured to read information of a memory card inserted into the card insertion hole and generates a result. The display panel displays the result to remind the user to operate the cosmetic instrument.

9 Claims, 5 Drawing Sheets

(51) Int. Cl.
  *A61H 23/02* (2006.01)
  *A45D 34/04* (2006.01)
  *A45D 34/06* (2006.01)
  *A61H 99/00* (2006.01)
  *A61N 5/06* (2006.01)
  *A61N 1/04* (2006.01)
  *A61N 1/32* (2006.01)

(52) U.S. Cl.
  CPC .............. *A61N 1/044* (2013.01); *A61N 1/328* (2013.01); *A61N 2005/0626* (2013.01); *A61N 2005/0644* (2013.01); *A61N 2005/0651* (2013.01); *A61N 2005/0663* (2013.01)

(56) References Cited

U.S. PATENT DOCUMENTS

| | | | |
|---|---|---|---|
| 6,672,341 B2 * | 1/2004 | Bartholomew | A45D 44/00 141/104 |
| 6,712,704 B2 * | 3/2004 | Eliott | A63F 13/12 463/41 |
| 7,786,626 B2 * | 8/2010 | Reishus | H02K 33/16 15/22.1 |
| 9,737,709 B2 * | 8/2017 | Bachinski | A61N 1/36021 |
| 2003/0041253 A1 * | 2/2003 | Matsui | G06F 12/0246 713/189 |
| 2005/0020947 A1 * | 1/2005 | Dehli | A61F 7/00 601/16 |
| 2008/0200849 A1 * | 8/2008 | Hollington | A61H 15/0078 601/46 |
| 2009/0099413 A1 * | 4/2009 | Kobashikawa | A61H 19/34 600/38 |
| 2015/0141884 A1 * | 5/2015 | Thiebaut | A61H 7/00 601/112 |
| 2016/0206087 A1 * | 7/2016 | Skidmore | A46B 13/008 |
| 2016/0328991 A1 * | 11/2016 | Simpson | A61B 5/742 |
| 2017/0156540 A1 * | 6/2017 | Wheatley | A47J 31/005 |
| 2017/0165439 A1 * | 6/2017 | Kaufmann | A61M 15/0041 |

* cited by examiner

COSMETIC INSTRUMENT CAPABLE OF READING MEMORY CARD

CROSS-REFERENCE TO RELATED APPLICATION

This present application claims the benefit of Chinese Patent Application No. 201510066325.4 filed on Feb. 7, 2015, the contents of which are hereby incorporated by reference.

BACKGROUND OF THE INVENTION

Field of the Invention

This disclosure relates to cosmetology field, and more particular, to a cosmetic instrument capable of reading a memory card.

Description of the Related Art

With continuous improvement of life quality, more and more people begin to pay attention to beauty, hope that their face glowing with health. From the beginning of twentieth century 90's, the scientific and technical personnel have begun to focus on the cosmetology industry, and being introducing more scientific knowledge, materials and equipment into cosmetology industry, so that the efficiency and safety index of cosmetic instruments has been greatly improved and developed. In recent years, compared with the traditional manual care for based nursing, the instrument care is more popular.

To a beauty salon for nursing is not only cost more money, but also need to take specific time. Therefore portable cosmetic instruments mainly used at home are developed, to facilitate people do personal care anywhere and anytime. However, at present traditional cosmetic instrument function is relatively simple, and cannot meet types of needs for consumers. Its main performance in: first, for some well-known brands cosmetic production sold in some counters, because of they are usually very expensive, therefore only a few people use these well-known brands cosmetic production and they do not know correct use method of the knowledge. The traditional cosmetic instruments cannot guide people how to do beauty care. Therefore, the majority of users cannot achieve the desired beauty effect. Second, the amount of each of these expensive cosmetic productions is little, if directly pressing the expensive cosmetic productions out to hands from the cosmetic packaging bags and then wiped to the face as the traditional way. It will waste a lot of cosmetic productions. And as we know, the outer epidermal layer and granular layer of human skin will prevent the cosmetics penetration. Therefore, if use amount at each time is too small, the cosmetic production cannot penetrate into enough depth of the human skin, cannot achieve beauty effect. Third, traditional cosmetic instruments cannot identify if the cosmetic production people bought is true or fake. When customers use fake production, good effect for the skin cannot reach but reversely it may cause harm to the skin.

It is desirable to provide a disclosure, which can overcome the problems and limitations mentioned above.

SUMMARY OF THE INVENTION

The present disclosure is directed to a cosmetic instrument capable of reading a memory card that substantially obviates one or more of the problems due to limitations and disadvantages of the related art.

In an aspect of the present invention, there is provided A cosmetic instrument capable of reading a memory card includes a first housing; a second housing, assembled with the first housing to cooperatively form a shell having a chamber; a massage head mounted on a first end of the shell, the massage head extending into the chamber; a control panel comprising a display panel, control panel being mounted on the shell beside the massage head; a micro controller unit and a drive unit positioned in the chamber and electrically connected with each other, the micro controller unit further being electrically connected to the control panel and the display panel; wherein the first housing and the seconding housing define a card insertion hole, the micro controller unit is configured to read information of a memory card inserted into the card insertion hole and generates a result; and the display panel displays the result to remind the user to operate the cosmetic instrument.

It is to be understood that both the foregoing general description and the following detailed description are exemplary and explanatory and are intended to provide further explanations of the invention as claimed.

DETAILED DESCRIPTION OF THE PREFERRED EMBODIMENTS

Figure 1:
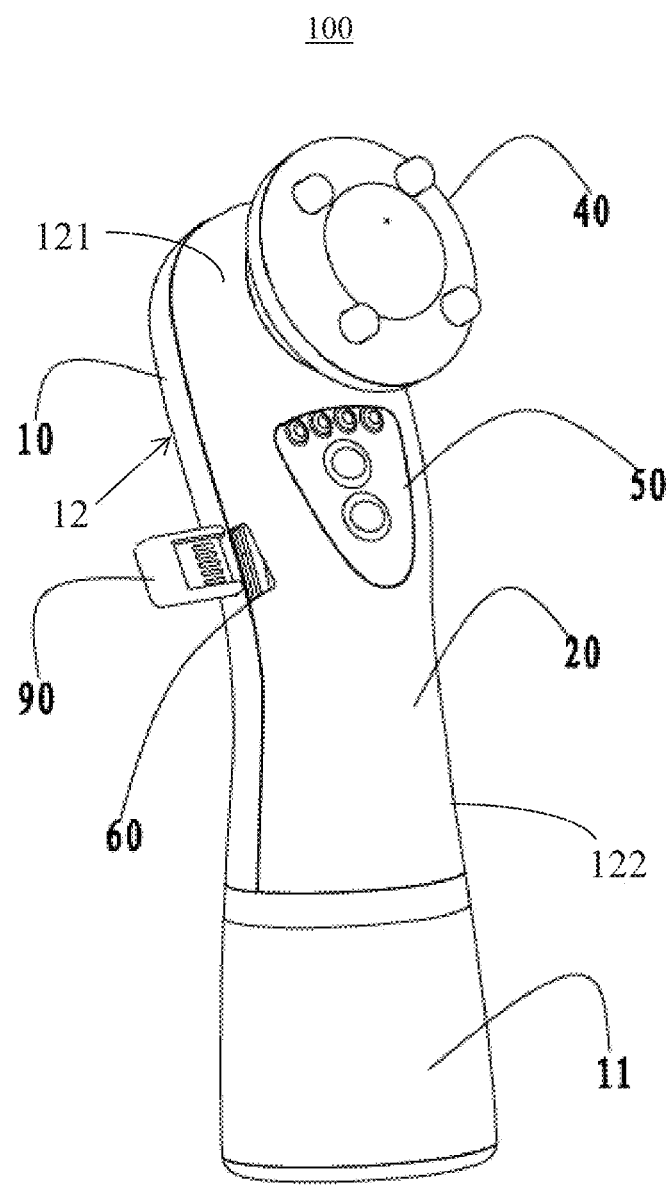
FIG. 1 is an isometric, schematic view of a cosmetic instrument with a memory card, according to a first embodiment of the present disclosure.
Figure 2:
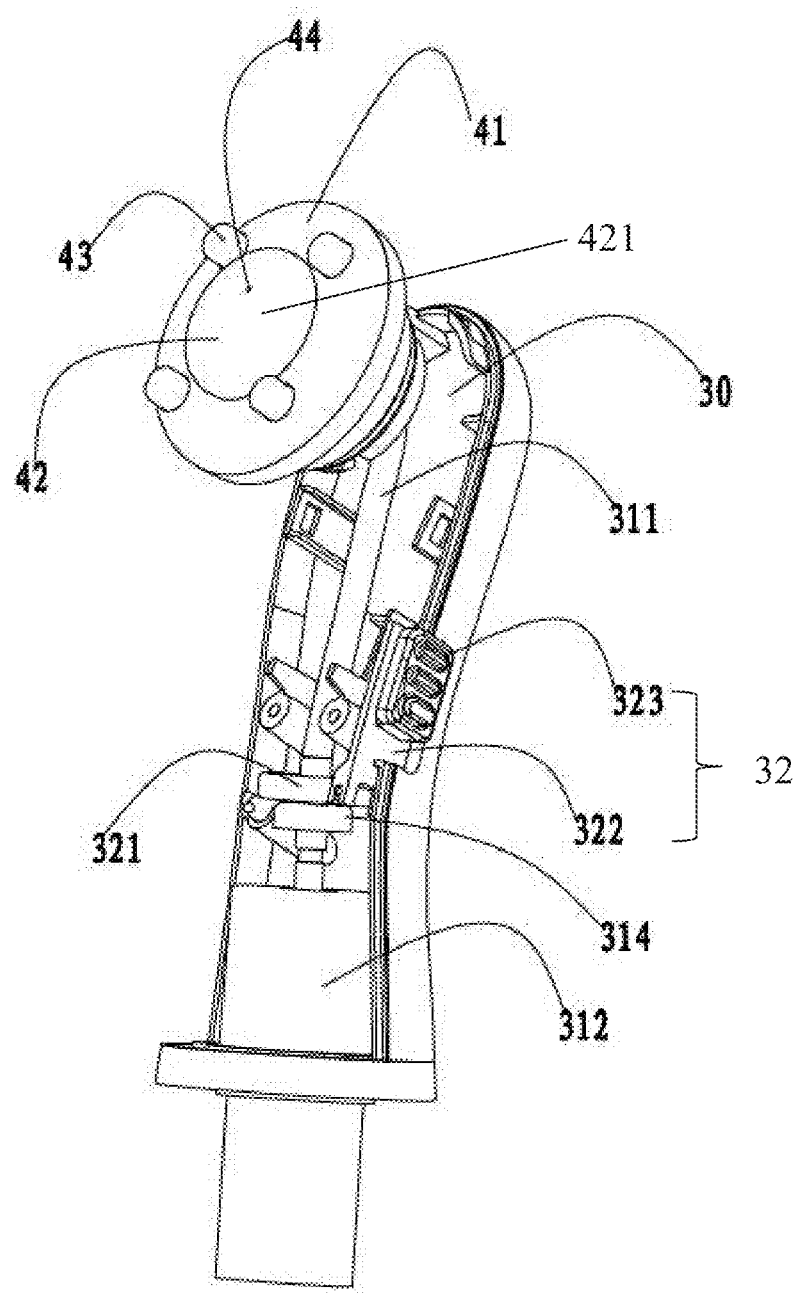
FIG. 2 is an isometric, is an isometric, schematic view of part of the cosmetic instrument of FIG. 1.
Figure 3:
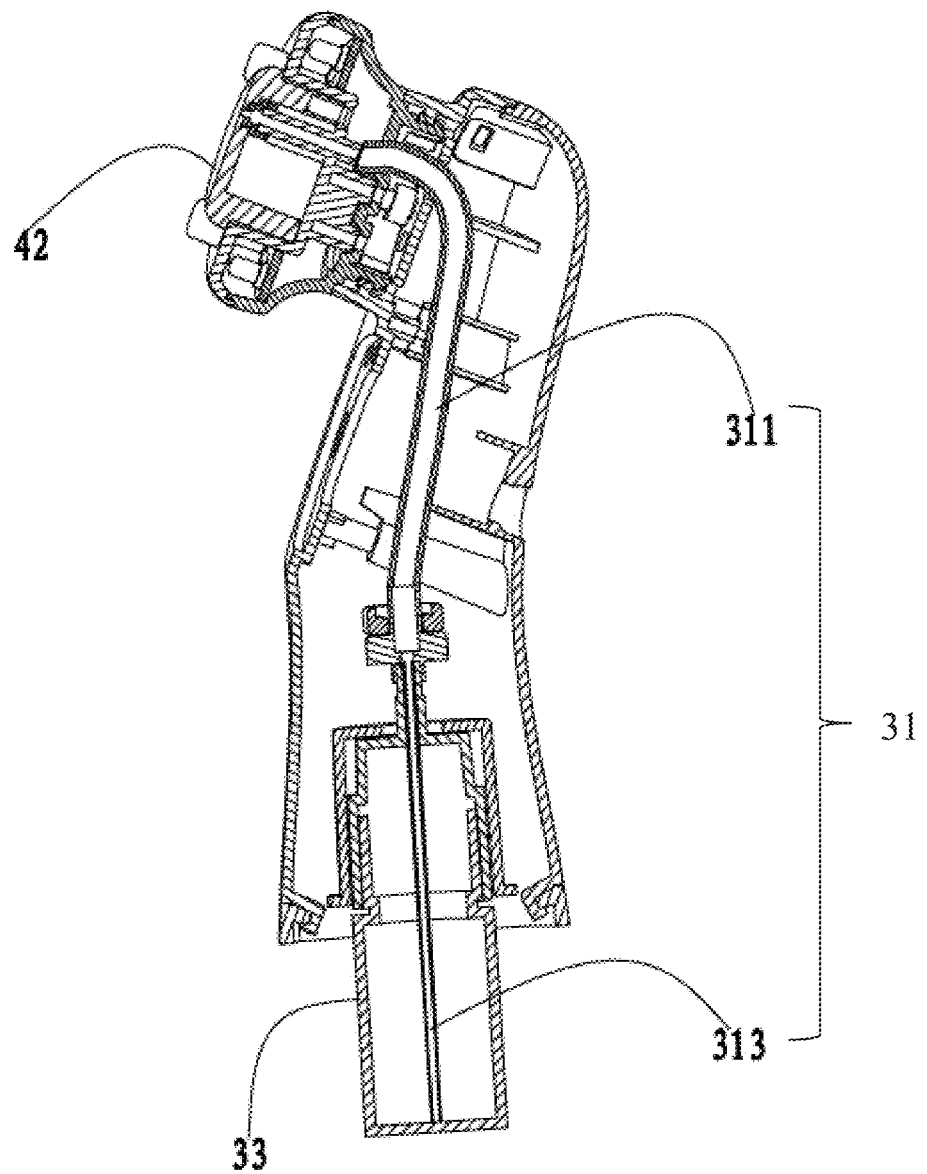
FIG. 3 is a cross-sectional view of the cosmetic instrument FIG. 1.
Figure 4:
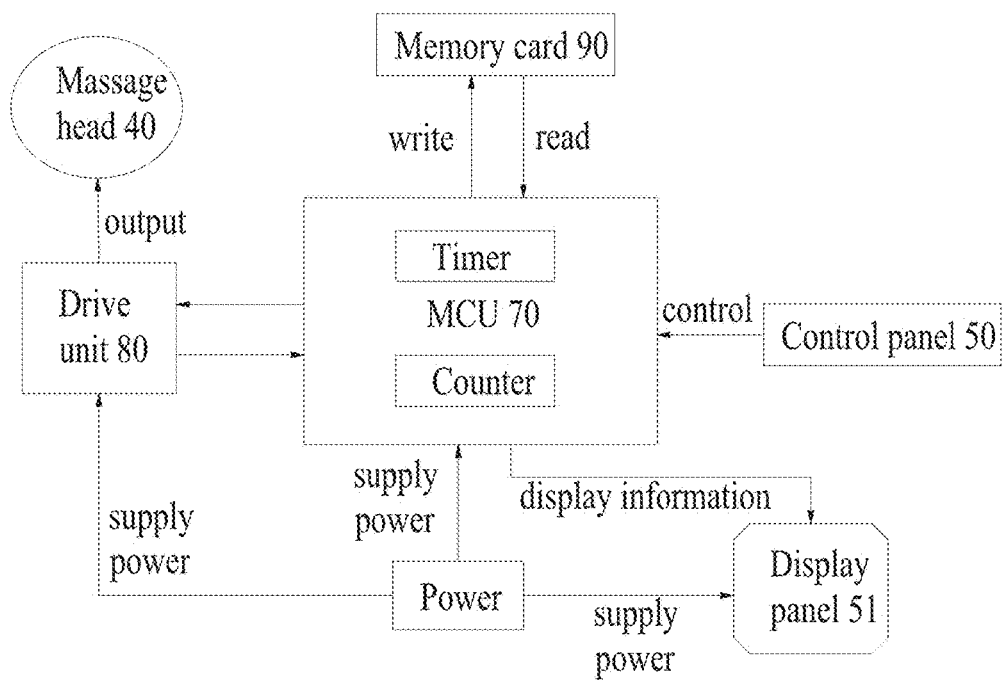
FIG. 4 is a block diagram of the cosmetic instrument of FIG. 1.
Figure 5:
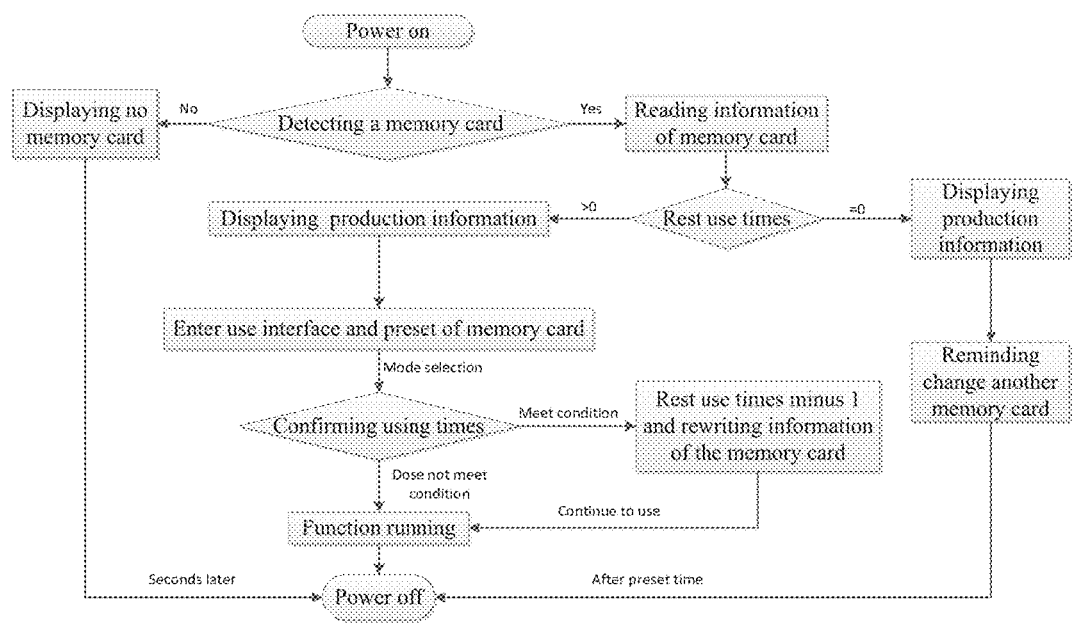
FIG. 5 is work flow chart of the cosmetic instrument of FIG. 1.

Referring to FIG. 1 to FIG. 5, a cosmetic instrument 100 capable of reading a memory card is provided, in according with the present disclosure. The cosmetic instrument 100 includes a first housing 10, a second housing 20, a massage head 40, a control panel 50, a micro controller unit (MCU) 70, a drive unit 80, and a power supply (not show).

The first housing 10 and the second housing 20 can be assembled together to form a general tubular shell 12. The first housing 10 and the second housing 20 cooperatively form a chamber 30. The shell 12 includes a first end 121 and a second 122. The massage head 40 is mounted the first end 121 of the shell 12. In the embodiment, the massage head 40 is mounted on the second housing 20. In alternative embodiments, the massage head 40 can be mounted on the first housing 10. The massage head 40 further extends into the chamber 30. The control panel 50 is mounted on the second housing 20 under or beside the massage head 40. The control panel 50 includes a display panel 51. The first housing 10 and the seconding housing 20 define a card insertion hole 60. It is means that one part of the card insertion hole 60 is defined in the first housing 10 and the other part of the card insertion hole 60 is defined in the second housing 20. In alternative embodiments, the card insertion hole 60 can be only defined in the first housing 10 or in the second housing 20.

The cosmetic instrument 100 further includes a bottom barrel 11 connected to the second end 122 of the shell 11. The bottom barrel 11 is hollow and in communication with the chamber 30 of the shell 12. The bottom barrel 11 can be assembled to the shell 12 by snap rings, screws, or joiner shackle.

The massage head 40 includes an annular base portion 41, a protrusion portion 42, a number of light emitting pearls (not show), and four electrodes 43. The protrusion portion 42 is positioned in the center of the base portion 41 and is cylindrical. One end of the protrusion portion 42 is closed to form a closed end 421. A number of piezoelectric ceramic plates (not show) are adhered to an inner surface of the closed end 421. The closed end 421 further defines a liquid passing hole 44. The liquid passing hole 44 passes through the closed end 421 thereof. The light emitting pearls can be light emitting diodes (LEDs). The light emitting pearls can provide three types of wavelength of light containing red, yellow, and blue light. According to requirement of different skin care, the light emitting pearls provide different combinations of the three types of wavelength of light. There is a light concentrating bowl (not show) positioned outside of the light emitting pearls for concentrating light. The electrodes 43 are configured for generating electromagnetic wave in a specific frequency. The electromagnetic wave can assist in cosmetic nutrients infiltrate into the skin. The light emitting pearls and the electrodes 43 are mounted on the annular base portion 41 surrounding the protrusion portion 42.

The cosmetic instrument 100 further includes a liquid outlet pump 31 mounted in the chamber 30. The liquid outlet pump 31 includes an outlet pipe 311, a main body 312, an inlet pipe 313, and a pressing pump head 314. One end of the outlet pipe 311 is connected to and communicated with the main body 312, and the other end of the outlet pipe 311 is connected to and communicated with the liquid passing hole 44. One end of the inlet pipe 312 is connected to and communicated with the main body 312, and the other end of the inlet pipe 312 is introduced into the bottom barrel 11. The main body 312 is substantially a hollow cube and positioned on the bottom barrel 11. The pressing pump head 314 is movable and presses on the outlet pipe 311 near the main body 312. The cosmetic instrument 100 further includes a pressing device 32 for driving the pressing pump head 314 move back and forth relative to the main body 312. The pressing device 32 includes a first connection arm 321, a second connection arm 322, and a pressing key 323. The first connection arm 321 and the second connection arm 322 are received in the shell 12. One end of the first connection arm 321 is connected to an inner surface of the shell 12. The first connection arm 321 is attached against the pressing head 314 and is rotable relative to the shell 12. The other end of the first connection arm 321 is connected to one end of the second connection arm 322. The pressing key 323 is mounted on the second pressing arm 322 and protrudes out of the shell 12. The pressing key 323 is slidable relative to the shell 12, such that the pressing key 322 drives the second connection arm 322 move, the second connection arm 322 drives the first connection rotate, and the first connection arm 321 drives the pressing pump head 314 move back and forth against the outlet pipe 311. The bottom barrel 11 is configured for receiving a cosmetic bottle 33 containing liquid cosmetic. The other end of the inlet pipe 313 which introduced into the bottom barrel 11 is inserted into the cosmetic bottle 33. Therefore, when sliding the pressing key 323, liquid cosmetic can be pumped to the liquid passing hole 44 via the inlet pipe 313, the main body 312, and the outlet pipe 311. Then liquid cosmetic flow to an outer surface of the closed end 421.

A memory card 90 is inserted into the card insertion hole 60 and electrically connected to a circuit board (not show) mounted in the shell 12. The MCU 70 also electrically connected to the circuit board. Therefore, the memory card 90 is electrically to the MCU 70. However, the memory card 90 is encrypted with an encryption key, and the MCU 70 is preset with a decryption key corresponding to the encryption key. The decryption key corresponding and the encryption key are match with each other. When the decryption key and the encryption key are matched with each other, then the MCU 70 can read information of the memory card 90 and start working procedure. The memory card 90 stores a great of information but at least includes commodity information of a cosmetic production, rest use times of the cosmetic production, use procedures of the cosmetic production, and use amount in each use procedure of the cosmetic. The commodity information can be manufacturer, production date, and brand, etc. The use procedures include use steps, required time of each step, etc.

The cosmetic instrument 100 works as following: when a user start the cosmetic instrument 100 (namely the cosmetic instrument 100 is powered on), the cosmetic instrument 100 will initialize and self-check and firstly determine whether the memory card 90 inserted into the card insertion hole 60 is a valid memory card. The valid memory card means that the decryption key of the MCU 70 and the encryption key of the memory card are matched with each other. If the memory card 90 inserted into the card insertion hole 60 is valid, namely the decryption key of the MCU 70 and the encryption key of the memory card are successfully matched with each other, then the cosmetic instrument 100 immediately comes into a standby state.

Then the MCU 70 reads information of the memory card 90 and confirms the rest use times of the cosmetic production, the display panel 51 displays the rest use times of the cosmetic production confirmed by the MCU 70. If the rest use times of the cosmetic production confirmed by the MCU 70 is zero (it is means that the memory card 90 cannot be used any more), the display panel 51 displays the rest use time being zero and further displays reminding information for changing another memory card. If the rest use times of the cosmetic production confirmed by the MCU 70 is not zero (it is means that the memory card 90 can be continue to use), the display panel 51 displays the rest use time, and the user can choose an automatically control mode or a manual mode for the follow-up beauty treatment according to their actual requirement through the display panel 51. Whether or not the rest use time of cosmetic production displayed by the display panel is zero, the display panel 51 will display commodity information of the cosmetic production. The MCU 70 generates leading information about commodity information of a cosmetic production, rest use times of the cosmetic production, use procedures of the cosmetic production, and use amount in each use procedure of the cosmetic. And the display panel 51 displays the leading information.

When the user chooses the manual mode, the user can operate function keys displaying on the display panel 51 (the display panel can be touch panel) of control panel 50. The MCU 70 triggers the drive unit 80 according input command from the function keys. The drive unit 80 outputs executing command to the massage head 40 and make the massage 40 into a work sate. Then the drive unit 80 sends feedback signal to the MCU 70. The MCU 70 processes the feedback signal and generate a result, the display panel 51 displays result to remind the user to operate the cosmetic instrument.

The display panel 51 then displays steps for follow-up beauty treatment to remind the user to operate until beauty treatment finish.

When the user chooses the automatically control mode, it is unnecessary for the user to operate function keys displaying on the display panel 51 of control panel 50. The MCU 70 directly read out procedure information from the memory card 90. The cosmetic instrument 100 automatically executes beauty treatment according to the procedure information.

No matter the user chooses the manual mode or the automatically control mode. The MCU 70 will record use time of the memory card 90 for beauty treatment, and rewrite the rest use time stored in the memory card 90. Therefore the MCU 70 can confirm the rest use time when the memory card 90 is inserted to the card insertion hole 60 at next time. The MCU 70 also has a timer used to record the time spent in each of the beauty treatment steps in order to control the time consuming of each of the beauty treatment steps.

By using the present disclosure cosmetic instrument 100, the user does not have to worry about how to use expensive cosmetic productions he/she bought. Therefore each cosmetic production can be matched with a memory card 90. As long as the user inserts the memory card 90 into the present disclosure cosmetic instrument 100, he/she can conveniently and efficiently finish beauty treatment according to operation leading displaying on the display panel 51. In addition, beauty treatment procedures stored in the memory card 90 are all best way to beauty researched and obtained by senior beauticians. Therefore so as long as the user has the cosmetic instrument 100, it is seems to have a full-time senior beautician carefully guide.

During the user using the cosmetic instrument 100, he/she can press the pressing key 323 to press out liquid cosmetic contained in the cosmetic bottle 33 according to reminding information displayed on the display panel. For example, the display panel 51 displays desired amount of the corresponding to times the user need to press the pressing key. It is greatly reduce loss of the liquid cosmetic in the cosmetic bottle 33. In addition, the valid memory card means that the decryption key of the MCU 70 and the encryption key of the memory card are matched with each other, therefore, cosmetic production made by a well-known cosmetic manufacturer can be matched with the memory card 90, and the cosmetic instrument 100 can be used only by the well-known cosmetic manufacture authorizing encryption key to the memory card. If the user bought fake cosmetic production not made by the well-known cosmetic manufacture, because these production are not matched with the correct memory card (namely authorized by the well-known cosmetic manufacturer), the cosmetic instrument 100 cannot be used (does not work). Therefore, as long as the user has the cosmetic instrument 100 authorized by a certain cosmetic manufacturer, he/she can effectively avoid buying fake and the cosmetics manufacturers of counterfeit products.

It will be apparent to those skilled in the art that various modification and variations can be made in the multicolor illumination device and related method of the present invention without departing from the spirit or scope of the invention. Thus, it is intended that the present invention cover modifications and variations that come within the scope of the appended claims and their equivalents.

What is claimed is:

1. A cosmetic instrument capable of reading a memory card, comprising:
   a first housing;
   a second housing, assembled with the first housing to cooperatively form a shell having a chamber;
   a massage head mounted on a first end of the shell, the massage head extending into the chamber;
   a control panel comprising a display panel, control panel being mounted on the shell beside the massage head;
   a micro controller unit and a drive unit positioned in the chamber and electrically connected with each other, the micro controller unit further being electrically connected to the control panel and the display panel;
   wherein the first housing and the second housing define a card insertion hole, the micro controller unit is configured to read information of a memory card inserted into the card insertion hole and generate leading information for a user; the user presses function keys according to the leading information displayed on the display panel; the micro controller unit triggers the drive unit according input command from the function keys; the drive unit outputs executing command to the massage head and sends feedback signal to the micro controller unit, the micro controller unit processes the feedback signal and generates a result; and the display panel displays the result to remind the user to operate the cosmetic instrument; wherein the massage head comprises an annular base portion, a protrusion portion, a number of light emitting pearls, and four electrodes; the protrusion portion is positioned in the center of the base portion and is cylindrical with one end closed to form an closed end; the light emitting pearls and the electrodes are mounted on the annular base portion surrounding the protrusion portion.

2. The cosmetic instrument capable of reading a memory card of claim 1, wherein a number of piezoelectric ceramic plates are adhered to an inner surface of the closed end; the closed end further defines a liquid passing hole.

3. The cosmetic instrument capable of reading a memory card of claim 2, wherein the cosmetic instrument further comprises a liquid outlet pump mounted in the chamber; the liquid outlet pump comprises an outlet pipe, a main body, an inlet pipe, and a pressing pump head; a first end of the outlet pipe is connected and communicated with the main body, and a second end of the outlet pipe is connected and communicated with the liquid passing hole; a first end of the inlet pipe is connected and communicated with the main body; the pressing pump head is movable and presses on the outlet pipe adjacent to the main body.

4. The cosmetic instrument capable of reading a memory card of claim 3, wherein the cosmetic instrument further comprises a pressing device for driving the pressing pump head to move back and forth relative to the main body.

5. The cosmetic instrument capable of reading a memory card of claim 4, wherein the pressing device comprises a first connection arm, a second connection arm, and a pressing key; the first connection arm and the second connection arm are received in the shell; a first end of the first connection arm is connected to an inner surface of the shell; the first connection arm is attached against the pressing pump head and is rotatable relative to the shell, a second end of the first connection arm is connected to a first end of the second connection arm; the pressing key is mounted on the second connection pressing arm and protrudes out of the shell, the pressing key is slidable relative to the shell, such that the pressing key drives the second connection arm to move, the second connection arm drives the first connection arm to rotate, and the first connection arm drives the pressing pump head to move back and forth against the outlet pipe.

6. The cosmetic instrument capable of reading a memory card of claim 3, wherein the cosmetic instrument further comprises a bottom barrel connected to a second end of the shell; a second end of the inlet pipe is introduced into the bottom barrel.

7. The cosmetic instrument capable of reading a memory card of claim 6, wherein the bottom barrel is configured for receiving a cosmetic bottle containing liquid cosmetic, the second end of the inlet pipe which introduced into the bottom barrel is inserted into the cosmetic bottle.

8. The cosmetic instrument capable of reading a memory card of claim 1, wherein the memory card is encrypted with an encryption key, and the micro controller unit is preset with a decryption key corresponding to the encryption key, the decryption key and the encryption key are matched with each other.

9. The cosmetic instrument capable of reading a memory card of claim 1, wherein the memory card stores information that at least comprises commodity information of a cosmetic, rest use times of the cosmetic, use procedures of the cosmetic, and use amount in each use procedure of the cosmetic.

* * * * *